United States Patent
Guskey et al.

(12) 
(10) Patent No.: US 6,297,203 B1
(45) Date of Patent: *Oct. 2, 2001

(54) STYLING SHAMPOO COMPOSITIONS CONTAINING CATIONIC STYLING POLYMERS AND CATIONIC DEPOSITION POLYMERS

(75) Inventors: Susan Marie Guskey, Montgomery; Christine Hall, Cincinnati, both of OH (US); Douglas Allan Royce, Aurora; Kimberly Ann Schoch, Lawrenceburg, both of IN (US)

(73) Assignee: The Procter & Gamble, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/851,292

(22) Filed: May 5, 1997

(51) Int. Cl.$^7$ .................................................. C11D 1/94
(52) U.S. Cl. ...................................................... 510/124
(58) Field of Search .................................. 510/122, 123, 510/125, 126, 127, 124

(56) References Cited

U.S. PATENT DOCUMENTS

| | | | |
|---|---|---|---|
| 3,679,754 | 7/1972 | Beereboom | 260/587 |
| 4,438,095 | * 3/1984 | Grollier et al. | 424/70 |
| 4,812,253 | * 3/1989 | Small et al. | 252/132 |
| 4,820,447 | * 4/1989 | Medcalf, Jr. et al. | 252/117 |
| 4,963,348 | 10/1990 | Bolich, Jr. et al. | 424/71 |
| 5,120,532 | 6/1992 | Wells et al. | 424/70 |
| 5,135,747 | 8/1992 | Faryniarz et al. | 424/401 |
| 5,190,915 | 3/1993 | Behan et al. | 512/2 |
| 5,344,643 | * 9/1994 | Thiel et al. | 424/70 |
| 5,378,731 | 1/1995 | Andrews et al. | 514/552 |
| 5,501,805 | 3/1996 | Behan et al. | 252/8.6 |
| 5,540,853 | * 7/1996 | Trinh et al. | 510/101 |
| 5,554,588 | 9/1996 | Behan et al. | 512/1 |
| 5,567,428 | * 10/1996 | Hughes | 424/401 |
| 5,624,666 | * 4/1997 | Coffindaffer et al. | 424/70.21 |
| 5,632,998 | * 5/1997 | Midha et al. | 424/401 |
| 5,648,323 | * 7/1997 | Coffindaffer et al. | 510/122 |
| 5,656,257 | * 8/1997 | Fealy et al. | 424/70.13 |
| 5,662,892 | * 9/1997 | Bolich, Jr. et al. | 424/70.1 |
| 5,679,324 | 10/1997 | Lisboa et al. | 424/45 |

* cited by examiner

Primary Examiner—John Hardee
(74) Attorney, Agent, or Firm—Linda M. Sivik; Armina E. Matthews; Joan B. Tucker

(57) ABSTRACT

Disclosed are styling shampoo compositions with improved styling performance, and which comprise (a) from about 5% to about 50% by weight of a surfactant component selected from the group consisting of a combination of an anionic surfactant and an amphoteric surfactant, and a combination of an anionic surfactant and a zwitterionic surfactant; (b) from about 0.025% to about 3% by weight of a cationic deposition polymer having a cationic charge density of from about 0.2 meq/gram to about 2 meq/gram and which is selected from the group consisting of cationic cellulose polymers, cationic guar gum derivatives, and mixtures thereof, (c) from about 0.5% to about 10% by weight of an organic cationic hair styling polymer having a cationic charge density of greater than about 2 meq/gram to less than about 4.75 meq/gram; and (d) from about 27% to about 94.5% by weight water. Especially effective are those styling shampoo compositions containing a combination of Polyquaternium-16 as the cationic styling polymer, Polyquaternium-10 as a cationic deposition polymer, and a surfactant matrix comprising a combination of ammonium laureth sulfate and cocoamidopropyl betaine.

19 Claims, No Drawings

STYLING SHAMPOO COMPOSITIONS CONTAINING CATIONIC STYLING POLYMERS AND CATIONIC DEPOSITION POLYMERS

FIELD OF THE INVENTION

The present invention relates to styling shampoo compositions which contain select combinations of cationic deposition polymer and cationic styling polymers to improve the styling performance of the composition, especially when used in select surfactant matrices such as combinations of zwitterionic and anionic surfactants.

BACKGROUND OF THE INVENTION

Many hair shampoo compositions provide acceptable cleaning but provide little or no styling benefits, e.g., body, hold, curl retention, stiffness. To realize such benefits, separate cleaning and styling products are often used.

Recently, hair shampoo compositions have been developed which can provide cleaning and styling performance from a single product. Many of these products contain styling polymers in a compatible shampoo base. To prepare such products, styling polymers can be incorporated into the shampoo base by first dissolving the polymer in a liquid carrier and then adding the polymer/liquid carrier premix to the surfactant phase of the composition. Alternatively, the styling polymer can be dispersed in the surfactant phase of the shampoo composition, and deposited onto the hair to form a thin film on the hair shaft. The polymers provide improved hairstyle benefits such as body, hold, and curl retention. However, some styling polymers, whether deposited onto the hair via a liquid carrier or by dispersion, leave the hair feeling sticky or tacky.

It has now been found that a combination of cationic deposition polymers and select organic cationic styling polymers can be incorporated into shampoo compositions containing select surfactant matrices to improve the styling performance of such compositions. This combination is especially effective in providing both conditioning and styling performance without leaving the hair feeling unduly coated, dirty, sticky, or tacky to the touch. The organic cationic styling polymers defined herein are especially effective in helping provide wet hair conditioning as well as hair styling performance when used in combination with the shampoo matrix defined herein.

In view of the foregoing, it is therefore an object of the present invention to provide a styling shampoo composition with improved styling performance. It is a further object of the present invention to provide improved hairstyle benefits such as hold, body, and curl retention from a styling shampoo composition containing a combination of cationic deposition polymer and organic cationic styling polymer. It is yet another object of the present invention to provide such a composition that also provides some hair conditioning benefits without leaving the hair feeling unduly coated, dirty, sticky or tacky to the touch.

SUMMARY OF THE INVENTION

The present invention is directed to styling shampoo compositions which comprise from (a) from about 5% to about 50% by weight of a surfactant component selected from the group consisting of a combination of an anionic surfactant and an amphoteric surfactant, and a combination of an anionic surfactant and a zwitterionic surfactant; (b) from about 0.025% to about 3% by weight of a cationic deposition polymer having a cationic charge density of from about 0.2 meq/gram to about 2 meq/gram and which is selected from the group consisting of cationic cellulose polymers, cationic guar gum derivatives, and mixtures thereof; (c) from about 0.5% to about 10% by weight of an organic cationic hair styling polymer having a cationic charge density of greater than about 2 meq/gram to less than about 4.75 meq/gram; and (d) from about 27% to about 94.5% by weight water.

It has been found that select organic cationic styling polymers, preferably Polyquaternium-16, can provide improved styling performance from a shampoo composition when used in combination with a cationic deposition polymer, especially when the cationic polymer combination is also used in combination with select surfactant combinations in the shampoo composition defined herein. The organic cationic styling polymers provide styling benefits such as improved body, hold, and curl retention.

DETAILED DESCRIPTION OF THE INVENTION

The styling shampoo compositions of the present invention comprise organic cationic styling polymers which provide the composition with improved styling performance. The styling polymers herein are soluble in water or dispersible in the surfactant phase of the shampoo composition.

The term "water-soluble" as used herein refers to any material that is sufficiently soluble in water to form a substantially clear solution to the naked eye at a concentration of about 0.2% by weight, preferably at about 0.5% by weight, even more preferably at about 1.0% by weight of the material in water at 25° C.

The term "water-insoluble" as used herein refers to any material that is not sufficiently soluble in water to form a substantially clear solution to the naked eye at a concentration of about 0.2% by weight, preferably at about 0.1% by weight of the insoluble material at 25° C.

The styling shampoo compositions of the present invention can comprise, consist of, or consist essentially of the elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

Surfactant Component

The styling shampoo compositions of the present invention comprise a surfactant component to provide cleaning performance to the composition. The surfactant component in turn comprises a combination of an anionic surfactant and a zwitterionic surfactant, or a combination of an anionic surfactant and an amphoteric surfactant. Such surfactants should be physically and chemically compatible with the essential components described herein, or should not otherwise unduly impair product stability, aesthetics or performance.

Suitable anionic surfactants for use in the styling shampoo composition herein include those which are known for use in hair care or other personal care cleansing compositions. The concentration of the anionic surfactant in the styling shampoo composition should be sufficient to provide the desired cleaning and lather performance, and generally ranges from about 5% to about 50%, preferably from about 6% to about 30%, more preferably from about 7% to about 25%, even more preferably from about 8% to about 18%, by weight of the composition.

Preferred anionic surfactants suitable for use in the styling shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having,, for example, an average of 3 moles of ethylene oxide per mole of alcohol, is sulfated and neutralized.

Specific nonlimiting examples of alkyl ether sulfates which may be used in the styling shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Nonlimiting examples of such surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic surfactants suitable for use in the styling shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxyalkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A nonlimiting example of such an alpha-olefin sulfonate mixture is described in U.S. Pat. No. 3,332,880, which description is incorporated herein by reference.

Another class of anionic surfactants suitable for use in the styling shampoo compositions are the beta-alkyloxy alkane sulfonates. These surfactants conform to the formula

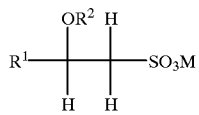

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic surfactants for use in the styling shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Suitable amphoteric or zwitterionic surfactants for use in the styling shampoo composition herein include those which are known for use in hair care or other personal care cleansing compositions. Concentrations of such amphoteric surfactants preferably range from about 0.5% to about 20%, preferably from about 1% to about 10%, by weight of the composition. Nonlimiting examples of suitable zwitterionic or amphoteric surfactants are described in U.S. Pat. Nos. 5,104,646 (Bolich Jr. et al.), 5,106,609 (Bolich Jr. et al.), which descriptions are incorporated herein by reference.

Amphoteric surfactants suitable for use in the styling shampoo composition are well known in the art, and these surfactants are most effective when used in combination with the anionic surfactants described herein. Nonlimiting examples of suitable amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric surfactants for use in the styling shampoo composition of the present invention include cocoamphoacetate, cocoamphodiacetate, lauroamphoacetate, lauroamphodiacetate, and mixtures thereof. Luroamphoacetate is the most preferred.

Zwitterionic surfactants suitable for use in the styling shampoo composition are well known in the art. Preferably the zwitterionic surfactants are used in combination with the anionic surfactants described herein, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Nonlimiting examples of suitable zwitterionic surfactants are the betaines including the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

Most preferred are surfactant systems comprising a surfactant combination of ammonium laureth sulfate and cocoamidopropyl betaine, especially when used in combination with Polyquaternium-16 as a cationic styling polymer and Polyquaternium-10 as a cationic deposition polymer (both polymers described in detail hereinafter). The surfactant combination of ammonium laureth sulfate and cocoamidopropyl betaine is preferably included in the styling shampoo composition at a weight ratio of ammonium laureth sulfate to cocoamidopropyl betaine of at least about 1.5:1, more preferably at least about 2:1, but preferably not more than about 5:1, more preferably not more than about 10:1.

The styling shampoo compositions of the present invention may further comprise additional surfactants for use in combination with the anionic surfactant component described hereinbefore. Suitable optional surfactants include nonionic surfactants. Any such surfactant known in the art for use in hair or personal care products may be used, provided that the optional additional surfactant is also chemically and physically compatible with the essential components of the styling shampoo composition, or does not otherwise unduly impair product performance, aesthetics or stability. The concentration of the optional additional surfactants in the styling shampoo composition may vary with the cleansing or lather performance desired, the optional surfactant selected, the desired product concentration, the presence of other components in the composition, and other factors well known in the art.

Nonlimiting examples of other anionic, zwitterionic, amphoteric or optional additional surfactants suitable for use in the styling shampoo compositions are described in *McCutcheon's, Emulsifiers and Detergents,* 1989 Annual, published by M.C. Publishing Co., and U.S. Pat. Nos. 3,929,678, 2,658,072; 2,438,091; 2,528,378, which descriptions are incorporated herein by reference.

Cationic Deposition Polymer

The styling shampoo compositions of the present invention comprise an organic cationic deposition polymer as a deposition aid for the styling polymer component described hereinafter. Concentrations of the cationic deposition polymer preferably range from about 0.025% to about 3%, more preferably from about 0.05% to about 2%, even more preferably from about 0.1% to about 1%, by weight of the composition.

The cationic deposition polymer, excluding the cationic hair styling polymers described hereinafter, for use in the styling shampoo composition of the present invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the styling shampoo composition. The average molecular weight of the cationic deposition polymer is between about 10 million and about 5,000, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm, but also preferably less than about 3 meq/gm, more preferably less than about 2 meq/gm, at the pH of intended use of the styling shampoo composition, which pH will generally range from about pH 4 to about pH 9, preferably between about pH5 and about pH 8.

The charge density can be controlled and adjusted in accordance with techniques well known in the art. As used herein the "charge density" of the cationic polymers is defined as the number of cationic sites per polymer gram atomic weight (molecular weight), and can be expressed in terms of meq/gram of cationic charge. In general, adjustment of the proportions of amine or quaternary ammonium moieties in the polymer, as well as pH of the styling shampoo composition in the case of the amines, will affect the charge density.

Any anionic counterions can be use in association with the cationic deposition polymers so long as the polymers remain soluble in water, in the styling shampoo composition, or in a coacervate phase of the styling shampoo composition, and so long as the counterions are physically and chemically compatible with the essential components of the styling shampoo composition or do not otherwise unduly impair product performance, stability or aesthetics. Nonlimiting examples of such counterions include halides (e.g., chlorine, fluorine, bromine, iodine), sulfate and methlylsulfate.

The cationic nitrogen-containing moiety of the cationic deposition polymer is generally present as a substituent on all, or more typically on some, of the monomer units thereof. Thus, the cationic deposition polymer for use in the styling shampoo composition includes homopolymers, copolymers, terpolymers, and so forth, of quaternary ammonium or cationic amine-substituted monomer units, optionally in combination with non-cationic monomers referred to herein as spacer monomers. Nonlimiting examples of such polymers are described in the *CTFA Cosmetic Ingredient Dictionary*, 3rd edition, edited by Estrin, Crosley, and Haynes, (The Cosmetic, Toiletry, and Fragrance Association, Inc., Washington, D.C. (1982)), which description is incorporated herein by reference.

Nonlimiting examples of cationic deposition polymers for use in the styling shampoo composition include polysaccharide polymers, such as cationic cellulose derivatives. Suitable cationic polysaccharide polymers include those which conform to the formula

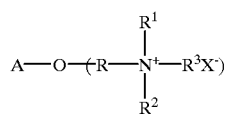

wherein A is an anhydroglucose residual group, such as a cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer JR and LR series of polymers with the most preferred being JR30M.

Other suitable cationic deposition polymers include cationic guar gum derivatives, such as guar hydroxypropyltrimonium chloride, specific examples of which include the Jaguar series (preferably Jaguar C-17) commercially available from Rhone-Poulenc Incorporated.

The cationic polymers herein are either soluble in the styling shampoo composition, or preferably are soluble in a complex coacervate phase in the styling shampoo composition formed by the cationic deposition polymer and the anionic surfactant component described hereinbefore. Complex coacervates of the cationic deposition polymer can also be formed with other charged materials in the styling shampoo composition.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5,6), 1988–89, pp 561–573, and D. J. Burgess, "Practical Analysis of Complex Coacervate Systems", *J. of Colloid anti Interface Science*, Vol. 140, No. 1, November 1990, pp 227–238, which descriptions are incorporated herein by reference.

It is believed to be particularly advantageous for the cationic deposition polymer to be present in the styling shampoo composition in a coacervate phase, or to form a coacervate phase upon application or rinsing of the shampoo to or from the hair. Complex coacervates are believed to more readily deposit on the hair which results in improved deposition of the styling polymer. Thus, in general, it is preferred that the cationic deposition polymer exist in the styling shampoo composition as a coacervate phase or form a coacervate phase upon dilution. If not already a coacervate in the styling shampoo composition, the cationic deposition polymer will preferably exist in a complex coacervate form in the shampoo upon dilution with water.

Techniques for analysis of formation of complex coacervates are known in the art. For example, microscopic analyses of the styling shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the styling shampoo composition.

Cationic Styling Polymer

The styling shampoo compositions of the present invention comprise an organic cationic hair styling, polymer suitable for application to human hair or skin, which is used in combination with the cationic deposition polymer described hereinbefore. The polymer can be soluble in water or dispersible in the surfactant components described hereinabove. These styling polymers for use herein are not unduly sticky or tacky to the touch, and provide hair styling benefits such as improved body and longer lasting curl. Concentrations of the styling, polymer range from about 0.5% to about 10%, preferably from about 1% to about 8%, more preferably from about 2% to about 6%, and even more preferably from about 2.5% to about 5%, by weight of the composition.

The organic cationic hair styling polymers useful herein have an open chain backbone which contains quaternary ammonium or cationic amino moieties, or combinations thereof. In order to achieve the optimal balance between styling performance and hair feel, the cationic charge density of the hair styling polymer should be less than about 4.75 meq/gram, preferably less than about 3.75 meq/gram, more preferably less than about 3 meq/gram. Furthermore, the charge density should be of a level such that efficient substantivity between the polymer and the hair can be attained, thereby preventing the hair from becoming unduly coated, sticky, or having an undesirably dirty feel. Preferably, the polymer has a cationic charge density of at least about 2 meq/gram, at the pH of the shampoo composition.

A nonlimiting example of suitable cationic hair styling polymers include copolymers of vinyl monomers having cationic amine or quaternary ammonium functionalities with water soluble space monomers such as N-vinyl pyrrolidone.

Other suitable cationic hair styling polymers include those cationic polymers containing or derived from quaternary ammonium monomers such as vinyl quaternary ammonium monomers having cyclic cationic nitrogen-containing rings such as imidazolium, e.g., alkyl vinyl imidazolium. The alkyl portions of these monomers are preferably lower alkyls such as the $C_1$–$C_3$ alkyls, more preferably $C_3$ and $C_2$ alkyls.

Preferred cationic hair styling polymers include copolymers of 1-vinyl-2-pyrrolidone and 1-vinyl-3-methylimidazolium salt (e.g., chloride salt) (referred to in the industry as Polyquaternium-16), such as those commercially available from BASF Wyandotte Corp. (Parsippany, N.J., USA) under LUVIQUAT tradename (e.g., LUVIQUAT FC 370, and LUVIQUAT FC 550). The most preferred cationic hair styling polymer is LUVIQUAT FC 370.

Water

The styling shampoo compositions of the present invention are aqueous systems which comprise from about 27% to about 94.5%, preferably from about 55% to about 85%, more preferably from about 60% to about 75%, of water by weight of the styling shampoo composition.

Optional Components

The styling shampoo compositions of the present invention may further comprise one or more optional components known or otherwise effective for use in hair care or personal care products, provided that the optional components are physically and chemically compatible with the essential component described herein, or do not otherwise unduly impair product stability, aesthetics or performance. Individual concentrations of such optional components may range from about 0.001% to about 10% by weight of the styling shampoo compositions.

Nonlimiting examples of optional components for use in the styling shampoo composition include perfumes, anti dandruff agents, hair conditioning agents (hydrocarbon oils, fatty esters, silicones), dyes, pearlescent aids, foam boosters, additional surfactants or nonionic cosurfactants, pediculocides, pH adjusting agents, preservatives, proteins, skin active agents, sunscreens, vitamins, and viscosity adjusting agents.

The styling shampoo composition of the present invention preferably further comprises a suspending or thickening agent. Suitable suspending agents for such materials are well known in the art, and include crystalline and polymeric suspending or thickening agents. Crystalline suspending agents are preferred, and include known acyl derivatives and amine oxides, and are described in U.S. Pat. No. 4,741,855, which description is incorporated herein by reference.

Nonlimiting examples of optional polymeric thickening agents for use in the styling shampoo composition include carboxyvinyl polymers, cellulose ethers, guar gum, polyvinyl alcohol, polyvinyl pyrrolidone, hydroxypropyl guar gum, starch and starch derivatives, and xantham gum. Suspending or thickening agents are described in U.S. Pat. Nos. 2,798,053, 4,686,254, 4,788,006, and 5,275,761, which description are incorporated herein by reference. The optional suspending or thickening agents are described in more detail hereinafter.

The styling shampoo composition of the present invention may further comprise a silicone hair conditioning agent, preferably a silicone hair conditioning agent in combination with an optional suspending agent for the silicone. The silicone hair conditioning agent is preferably non volatile, and is preferably present in the styling shampoo composition at concentrations ranging from about 0.01% to about 10% by weight of the styling shampoo composition. Nonlimiting examples of suitable silicone hair conditioning agents, and optional suspending agents for the silicone, are described in U.S. Reissue Pat. No. 34,584 (Grote et al.), U.S. Pat. Nos. 5,104,646 (Bolich Jr. et al.), 5,106,609 (Bolich Jr. et al.), which descriptions are incorporated herein by reference. The optional silicone hair conditioning agent, and optional suspending agents for the optional silicone, are described in more detail hereinafter Optional Silicone Hair Conditioning Agent The styling shampoo compositions of the present invention may further comprise an optional silicone hair conditioning agent at concentrations effective to provide hair conditioning benefits. Such concentrations range from about 0.01% to about 10%, preferably from about 0.10% to about 5%, more preferably from about 0.15% to about 3%, most preferably from about 0.2% to about 1%, by weight of the styling shampoo compositions.

The optional silicone hair conditioning agents are insoluble in the styling shampoo compositions, and are preferably nonvolatile. Typically it will be intermixed in the styling shampoo composition so as to be in the form of a separate, discontinuous phase of dispersed, insoluble particles, also referred to as droplets. These droplets are typically suspended with an optional suspending agent described hereinafter. The optional silicone hair conditioning agent phase will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46)) silicone conditioning agents are used (e.g. highly phenylated silicones).

The optional silicone hair conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The optional silicone hair conditioning agents for use in the styling shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, as measured at 25° C.

Optional silicone fluids include silicone oils which are flowable silicone materials having a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Optional silicone oils include polyalkyl or polyaryl siloxanes which conform to the following formula (I)

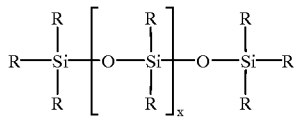

where R is aliphatic, preferably alkyl or alkenyl, or aryl, R can be substituted or unsubstituted, and x is an integer from 1 to about 8,000. Suitable unsubstituted R groups include alkoxy, aryloxy, arylalkyl, arylalkenyl, alkylamine, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the styling shampoo compositions, are chemically stable under normal use and storage conditions, are insoluble in the styling shampoo compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, arylalkyl, and alkylamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl -3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

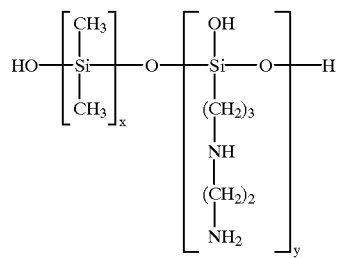

wherein x and y are integers. This polymer is also known as "amodimethicone".

Suitable cationic silicone fluids include those which conform to the formula (III) $(R_1)_a G_{3-a}$—Si—$(—OSiG_2)_n$—$(—OSiG_b(R_1)_{2-b})_m$—O—$SiG_{3-a}(R_1)_a$, wherein G is selected from the group consisting of hydrogen, phenyl, hydroxy, $C_1$–$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical conforming to the formula $CqH_{2q}L$ in which q is an integer 10 having a value of from 2 to 8 and L is selected from the following groups:

—$N(R_2)CH_2$—$CH_2$—$N(R_2)_2$

—$N(R_2)_2$

—$N(R_2)_3 A^-$

—$N(R_2)CH_2$—$CH_2$—$NR_2H_2 A^-$ in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

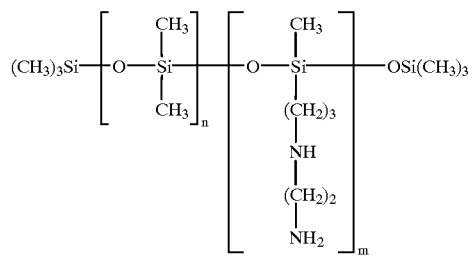

Other silicone cationic polymers which can be used in the styling shampoo compositions are represented by the formula (V):

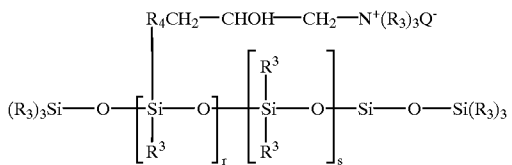

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference, the silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane) (methylvinylsiloxane) copolymer, and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (VI) below:

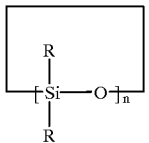

wherein R is as defined above, n is from about 3 to about 7, preferably from 3 to 5.

The high refractive index polysiloxane fluids contain a sufficient amount of aryl-containing, R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused Five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing, groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%. even more preferably at least about 35%., most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring, tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

References disclosing examples of some suitable silicone fluids for use in the styling shampoo compositions include U.S. Pat. Nos. 2,826,551, 3,964,500, 4,364,837, British Patent 849,433, and *Silicon Compound*, Petrarch Systems, Inc. (1984), all of which are incorporated herein by reference.

Silicone resins can be included in the silicone conditioning agent. These resins are highly crosslinked polymeric siloxane systems. The crosslinking, is introduced through the incorporation of trifunctionial and tetrafunctional silanies with monofunctional or difunctional, or both, silanes during, manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Optional Suspending Agent

The styling shampoo compositions of the present invention may further comprise a suspending agent at concentrations effective for suspending the optional silicone hair conditioning agent, or other water-insoluble material, in dispersed form in the styling shampoo compositions. Such concentrations range from about 0.1% to about 10%, preferably from about 0.3% to about 5.0%, by weight of the styling shampoo compositions.

Optional suspending agents include crystalline suspending agents that can be categorized as acyl derivatives, long chain amine oxides, or combinations thereof concentrations of which range from about 0.1% to about 5.0%, preferably from about 0.5% to about 3.0%, by weight of the styling shampoo compositions. When used in the styling shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the styling shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the styling shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B.F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the styling shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Method of Use

The styling shampoo compositions of the present invention are used in a conventional manner for cleansing and styling hair. An effective amount of the composition for cleansing and styling the hair is applied to the hair, that has preferably been wetted with water, and is then rinsed off. Such effective amounts preferably range from about 1 gm to about 50 gm, more preferably from about 3 gm to about 20 gm. Application to the hair typically includes working the composition through the hair such that most or all of the hair is contacted with the composition.

This method for cleansing and styling the hair comprises the steps of a) wetting the hair with water, b) applying an effective amount of the styling shampoo composition to the hair, c) shampooing the hair with the composition, and d) rinsing the composition from the hair with water. These steps can be repeated as many times as desired to achieve the cleansing and styling benefit desired. The method is preferably employed daily, every other day, or every third day, to provide and maintain the hair cleansing and styling performance described herein.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. The exemplified embodiments of the styling shampoo composition of the present invention provide both conditioning and styling performance without leaving the hair feeling unduly coated, dirty, sticky, or tacky to the touch. Ingredients are herein identified by chemical, trade, of CTFA name.

The styling shampoo compositions illustrated in Examples I–V are prepared by conventional formulation and mixing techniques, an example of which is set forth hereinbelow. All exemplified amounts are listed as weight percents and exclude minor materials such as diluents, filler, and so forth, unless otherwise specified.

Preparation

The styling shampoo compositions of the present invention may be prepared using conventional formulation and mixing techniques. The solid components are dispersed directly into a premix of the surfactants, or some portion of the surfactants which has been heated to melt the solid components. e.g., about 72° C. This mixture is then pumped through a high shear mill and cooled, and then the remaining components, including the cationic deposition polymer and the cationic styling polymer, are mixed in. The composition should have a final viscosity of from about 2,000 to about 15,000 cps, preferably from about 4,000 to about 10,000 cps. The viscosity of the composition can be adjusted using sodium chloride or ammonium xylenesulfonate as needed.

| | Weight % | | | | |
|---|---|---|---|---|---|
| Component | I | II | III | IV | V |
| Ammonium Laureth Sulfate | 9.5 | 9.0 | 9.3 | 9.3 | 9.5 |
| Ammonium Lauryl Sulfate | 1.0 | 3.0 | — | — | 1.0 |
| Lauroamphoacetate | 7.5 | 6.0 | — | — | 7.5 |
| Cocamidopropyl Betaine FB (4) | — | — | 4.7 | 4.7 | — |
| Polyquaternium-16 (Luviquat FC 370) (1) | 2.0 | 3.0 | 3.0 | 2.0 | 3.0 |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | 0.07 | — | 0.42 | 0.42 | 0.14 |
| Stearyl Alcohol | 0.03 | — | 0.18 | 0.18 | 0.06 |
| PEG-150 Pentaerythrityl Tetrastearate | 0.1 | 0.15 | — | 0.08 | 0.20 |
| Polyquaternium 10 (JR30M) (2) | 0.3 | — | 0.3 | — | 0.2 |
| Polyquaternium 10 (JR400) (2) | — | — | — | 0.4 | — |
| Guar Hydroxypropyl-trimonium Chloride (Jaguar C-17) (3) | — | 0.3 | — | — | — |
| Dimethicone | 0.25 | — | — | — | — |
| DMDM Hydantoin | 0.2 | 0.2 | 0.2 | 0.2 | 0.2 |
| Water | qs 100 | qs 100 | qs 100 | qs 100 | qs 100 |

(1) Available from BASF (Ludwigshafen, Germany)
(2) Available from Amerchol Corp. (Edison, NJ, USA)
(3) Available from Rhone-Poulenc (Cranbury, NJ, USA)
(4) Available from Goldschmidt (Hopewell, Virginia, USA)

What is claimed is:
1. A styling shampoo composition comprising:
   (a) from about 5% to about 50% by weight of a surfactant component selected from the group consisting of a combination of an anionic surfactant and an amphoteric surfactant, and a combination of an anionic surfactant and a zwitterionic surfactant;
   (b) from about 0.05% to about 2% by weight of a cationic deposition polymer having a cationic charge density of from 0.2 meq/gram to about 2 meq/gram and which is selected from the group consisting of cationic cellulose polymers, cationic guar gum derivatives, and mixtures thereof;
   (c) from about 2% to about 6% by weight of an organic cationic hair styling polymer having a cationic charge density of greater than 2 meq/gram to less than about 4.75 meq/gram; and
   (d) from about 27% to about 94.5% by weight water.

2. The composition of claim 1 wherein the composition comprises from about 2.5% to about 5% by weight of the organic cationic hair styling polymer having a charge density of greater than 2 meq/gram to less than about 3 meq/gram.

3. The composition of claim 2 wherein the organic cationic hair styling polymer is a copolymer of 1-vinyl-2-pyrrolidone and 1-vinyl-3-methylimidazolium salt.

4. The composition of claim 1 wherein the anionic surfactant is selected from the group consisting of ammonium lauryl sulfate, ammonium laureth sulfate, alkyl glyceryl ether sulfonate, and mixtures thereof; the amphoteric surfactant is selected from the group consisting of lauroamphoacetate, lauroamphodiacetate, cocoamphoacetate, cocoamphodiacetate, and mixtures thereof; and the zwitterionic surfactant is a betaine surfactant.

5. The composition of claim 4 wherein the betaine surfactant is cocoamidopropyl betaine.

6. The composition of claim 1 wherein the cationic cellulose polymer is Polyquaternium-10, and the guar gum derivative is guar hydroxypropyltrimonium chloride.

7. The composition of claim 1 wherein the composition further comprises a non-volatile hair conditioning agent selected from the group consisting of polyarylsiloxanes, polyalkylsiloxanes, polyalkylarylsiloxanes, derivatives thereof, and mixtures thereof.

8. The composition of claim 7 wherein the composition comprises from about 0.15% to about 3% by weight of a non-volatile polydimethylsiloxane as the hair conditioning agent.

9. A styling shampoo composition comprising:
   (a) from about 5% to about 50% by weight of a surfactant combination of ammonium laureth sulfate and cocoamidopropyl betaine having a weight ratio of ammonium laureth sulfate to cocoamidopropyl betaine of from about 1.5:1 to about 10:1;
   (b) from about 0.05% to about 2% by weight of a cationic deposition polymer having a cationic charge density of from 0.2 meq/gram to about 2 meq/gram and which is selected from the group consisting of cationic cellulose polymers, cationic guar gum derivatives, and mixtures thereof;
   (c) from about 2% to about 6% by weight of Polyquaternium-16 as a cationic hair styling polymer having a charge density of greater than 2 meq/gram to less than about 4.75 meq/gram; and
   (d) from about 27% to about 94.5% by weight of water.

10. The composition of claim 9 wherein the composition comprises from about 2.5% to about 5% by weight of the Polyquaternium-16 having a charge density of greater than 2 meq/gram to less than about 3 meq/gram.

11. The composition of claim 9 wherein the cationic cellulose polymer is Polyquaternium 10, and the guar gum derivative is guar hydroxypropyltrimonium chloride.

12. The composition of claim 9 wherein the weight ratio of ammonium laureth sulfate to cocoamidopropyl betaine is from about 1.5:1 to about 4:1.

13. The composition of claim 9 wherein the composition further comprises a non-volatile hair conditioning agent selected from the group consisting of polyarylsiloxanes, polyalkylsiloxanes, polyalkylarylsiloxanes, derivatives thereof, and mixtures thereof.

14. The composition of claim 13 wherein the composition comprises from about 0.15% to about 3% by weight of a non-volatile polydimethylsiloxane as the hair conditioning agent.

15. A method for cleansing and styling the hair, which method comprises the steps of:
   (a) wetting the hair with water,
   (b) applying from about 1 gram to about 50 grams of the composition of claim 1 to the hair,
   (c) shampooing the hair with the composition, and
   (d) rinsing the composition from the hair using water.

16. A method for cleansing and styling the hair, which method comprises the steps of:
   (a) wetting the hair with water,
   (b) applying from about 1 gram to about 50 grams of the composition of claim 9 to the hair,
   (c) shampooing the hair with the composition, and
   (d) rinsing the composition from the hair using water.

17. A styling shampoo composition comprising:
   (a) from about 5% to about 50% by weight of the composition of a surfactant component selected from the group consisting of a combination of a an anionic surfactant and an amphoteric surfactant, a combination of an anionic surfactant and a zwitterionic surfactant, and a combination of an anionic surfactant, an amphoteric surfactant, and a zwitterionic surfactant;
   (b) from about 0.05% to about 2% by weight of the composition of a cationic deposition polymer having a cationic charge density of from about 0.2 meq/gram to about 2 meq/gram and which is selected from the group consisting of cationic cellulose polymers, cationic guar gum derivatives, and mixtures thereof;
   (c) from about 2% to about 6% by weight of an organic cationic hair styling polymer having a cationic charge density of greater than about 2 meq/gram to less than about 4.75 meq/gram;
   (d) a suspending agent; and
   (e) from about 27% to about 94.5% by weight of the composition of water.

18. A styling shampoo composition according to claim 17 wherein the suspending agent is selected from the group consisting of crystalline suspending agents and combinations thereof.

19. A styling shampoo composition according to claim 18 wherein the composition comprises from about 0.1% to about 10% of the suspending agent.

* * * * *